(12) United States Patent
DeVaughn et al.

(10) Patent No.: US 6,723,528 B1
(45) Date of Patent: Apr. 20, 2004

(54) INOCULATION STORAGE ASSEMBLY AND METHOD FOR USE THEREOF

(75) Inventors: Donald H. DeVaughn, 4200 California St., Suite 100, San Francisco, CA (US) 94118; Wolfgang Ott, Antioch, CA (US)

(73) Assignee: Donald H. DeVaughn, San Francisco, CA (US)

( * ) Notice: Subject to any disclaimer, the term of this patent is extended or adjusted under 35 U.S.C. 154(b) by 0 days.

(21) Appl. No.: 10/280,694

(22) Filed: Oct. 28, 2002

(51) Int. Cl.[7] .................................................. C12Q 1/24
(52) U.S. Cl. .................. 435/30; 435/309.3; 73/864.16; 422/100
(58) Field of Search .................... 73/864.72, 864.13, 73/864.16; 435/309.1, 309.2, 309.3; 422/100; 604/38, 187, 208

(56) References Cited

U.S. PATENT DOCUMENTS

| | | | | |
|---|---|---|---|---|
| 3,147,197 A | * | 9/1964 | Connors | 435/309.3 |
| 3,772,154 A | * | 11/1973 | Isenberg et al. | 435/33 |
| 3,874,503 A | * | 4/1975 | Shaffer et al. | 206/205 |
| 3,915,806 A | * | 10/1975 | Horlach | 435/307.1 |
| 4,010,077 A | * | 3/1977 | Pardos | 435/309.3 |
| 4,657,869 A | * | 4/1987 | Richards et al. | 435/287.6 |
| 4,687,746 A | * | 8/1987 | Rosenberg et al. | 435/309.3 |
| 4,690,676 A | * | 9/1987 | Moulding et al. | 604/189 |
| 4,927,019 A | * | 5/1990 | Haber et al. | 206/365 |
| 5,048,684 A | * | 9/1991 | Scott | 206/364 |
| 5,330,899 A | | 7/1994 | DeVaughn | 435/30 |
| 6,245,559 B1 | | 6/2001 | DeVaughn et al. | 435/309.3 |

* cited by examiner

Primary Examiner—David A. Redding
(74) Attorney, Agent, or Firm—Dorsey & Whitney LLP

(57) ABSTRACT

An inoculation storage assembly and method of preserving sterility including an inoculation device (20), a storage rack or container (84, 184), and a handling tool (60, 160). The inoculation device (20) being an elongated ember (22) with a gripping section (24), an inoculation section (26), and a seal (25) carried by elongated member (22). The seal (25) preferably having an arcuate surface (19) for sealing engagement against a seal contact surface (162, 262) in a cavity (86, 186) in the storage rack (84, 184). The storage container (84, 184) including an open upper end or opening (88) and a seal contact surface (162, 262) dimensioned to sealingly receive the seal (25), with the inoculation device (20) being mounted in sealed relation to the cavity (86). A handling tool (60, 160) capable of releasable coupling to gripping section (24) of the inoculation device (20) is provided. A method of using the inoculation storage assembly and preserving sterility is also disclosed.

25 Claims, 7 Drawing Sheets

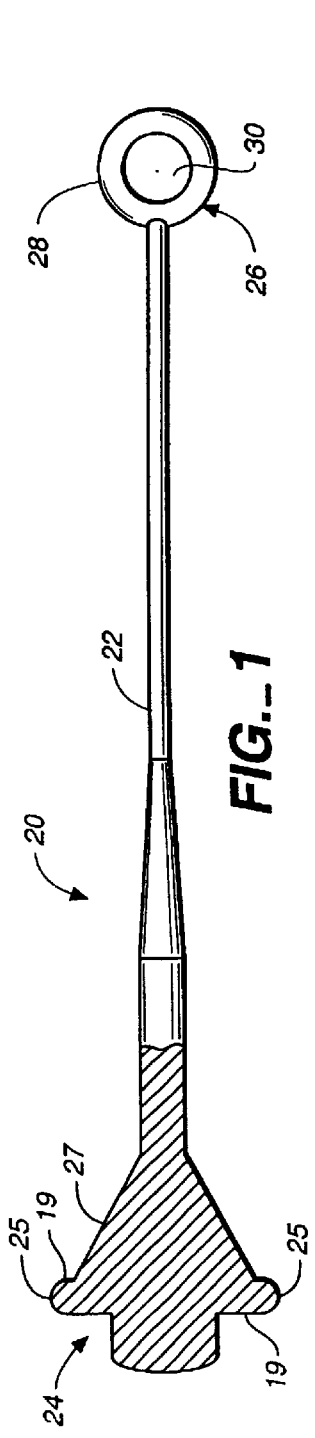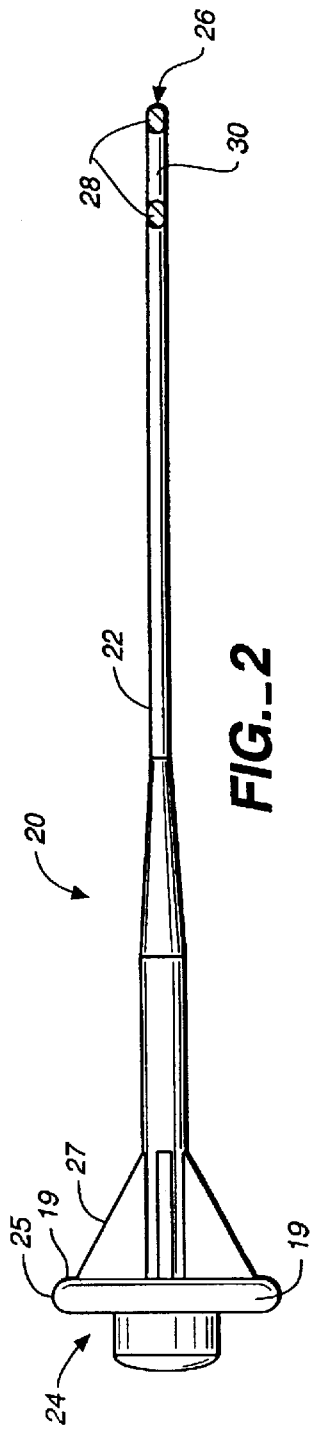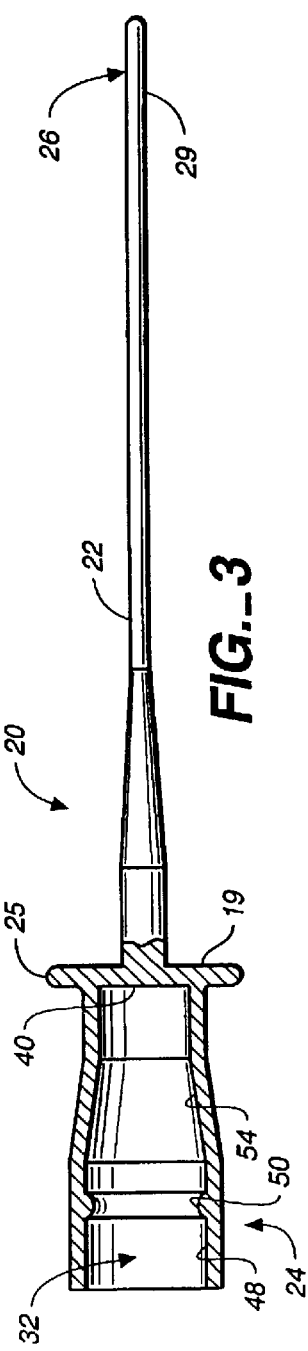

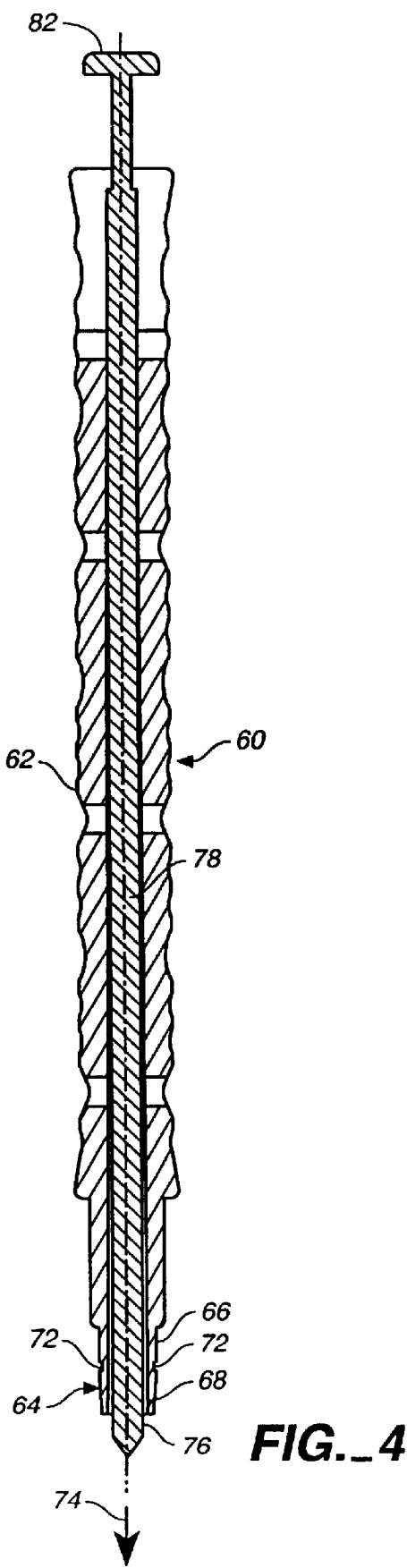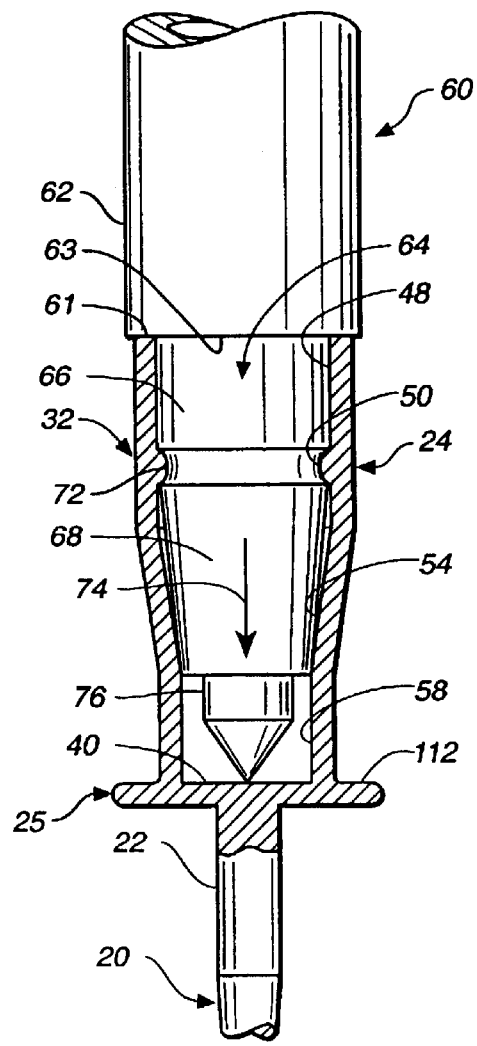
FIG._4  FIG._5

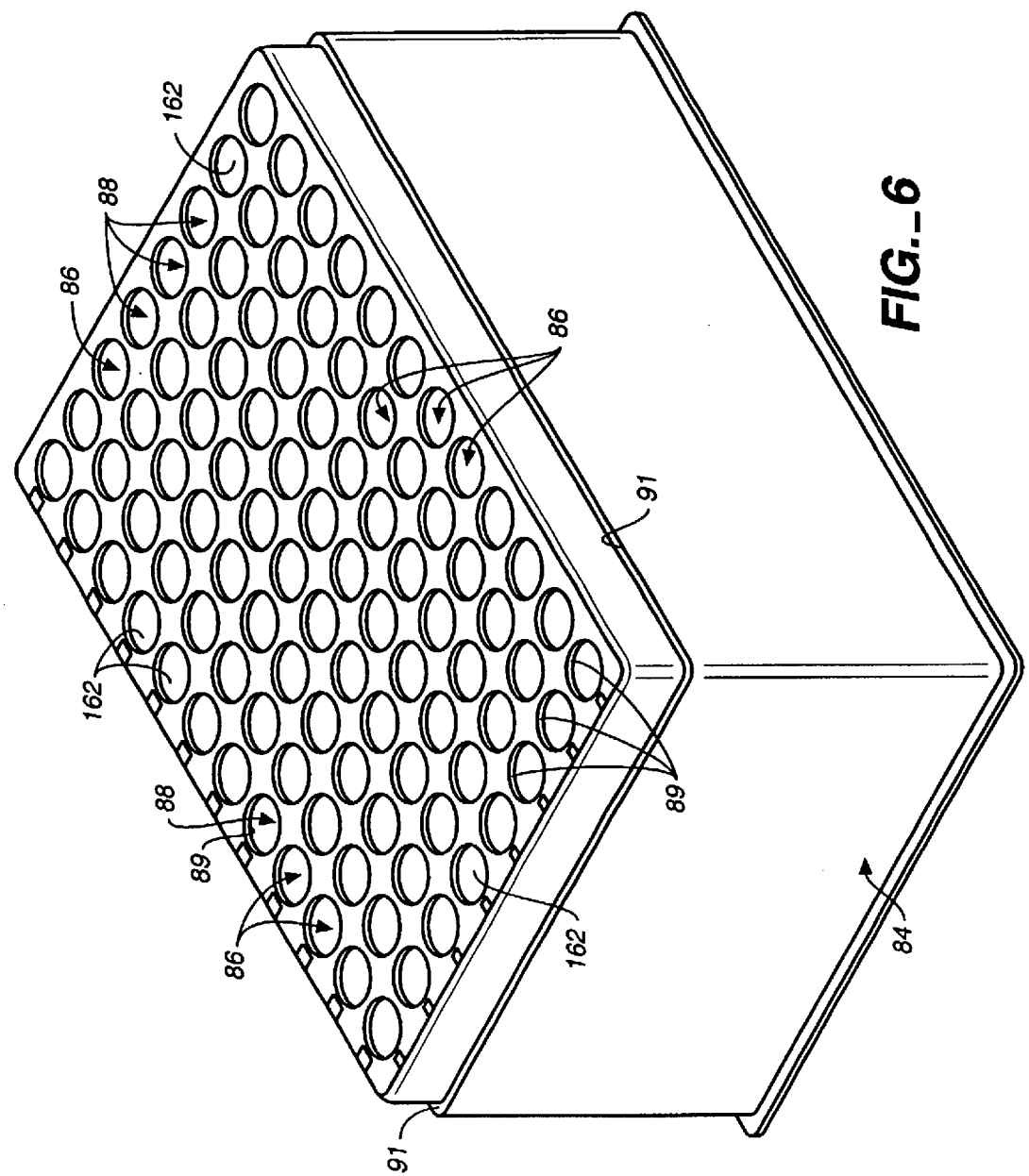

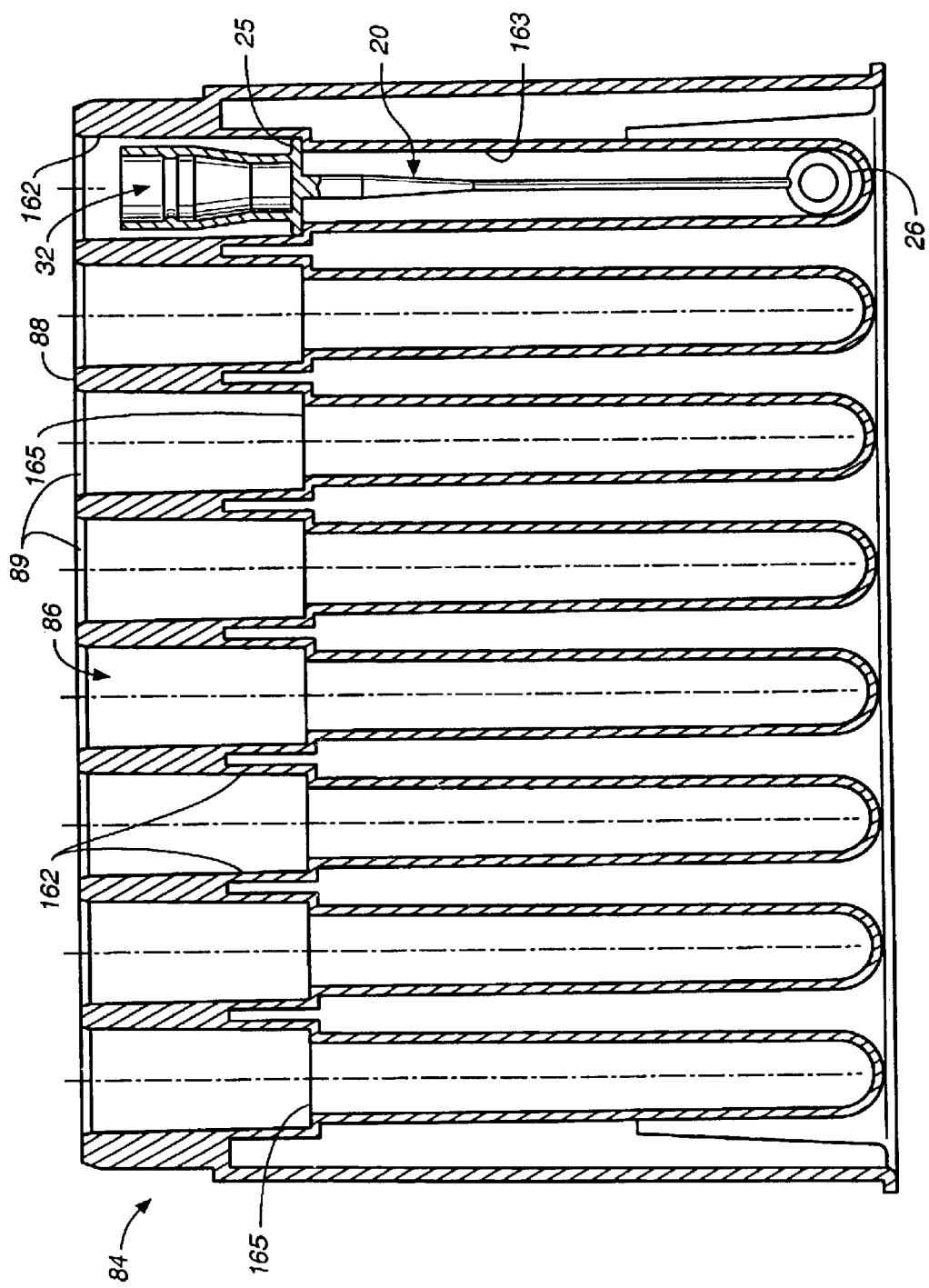
FIG._7

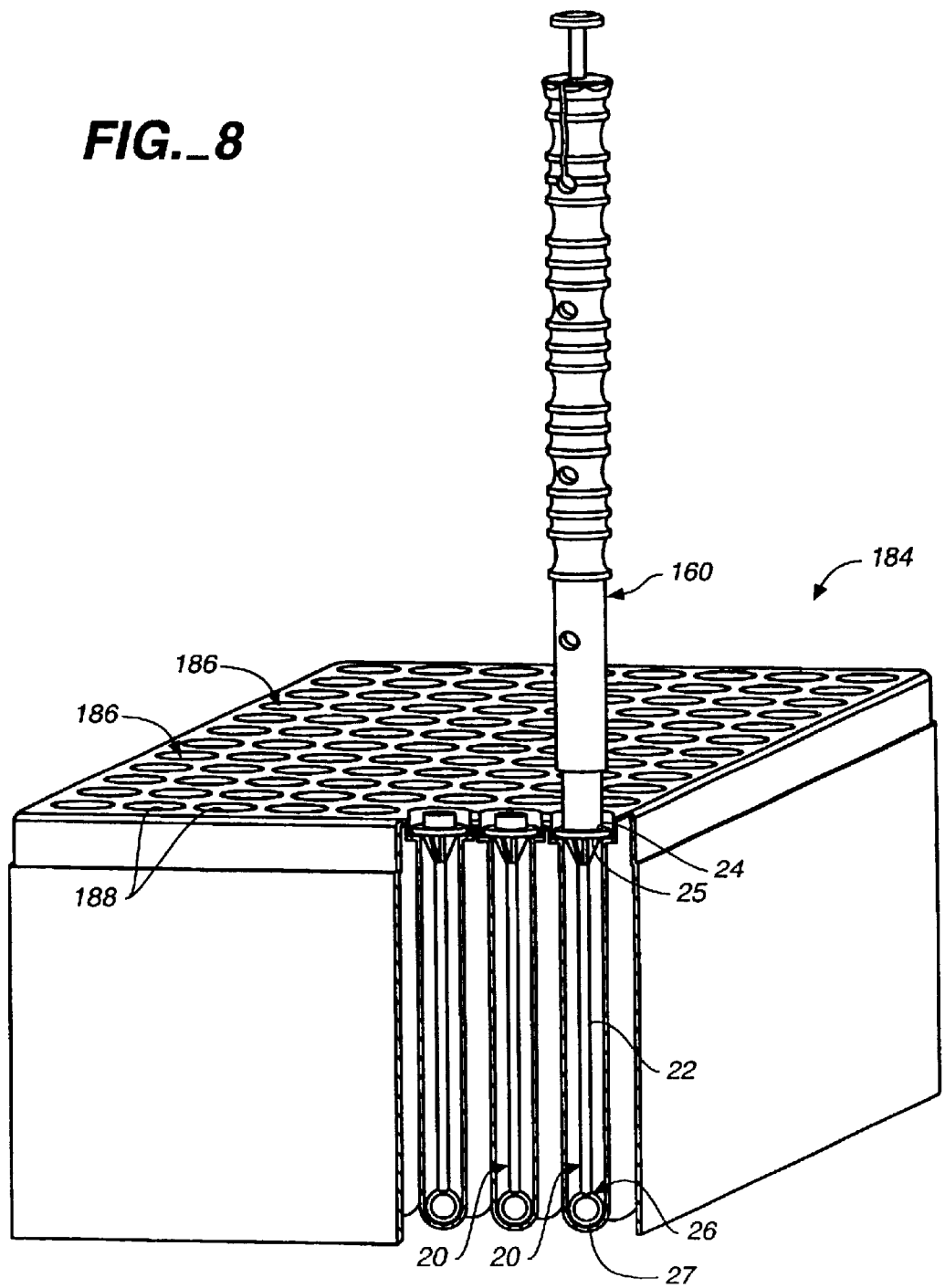
FIG._8

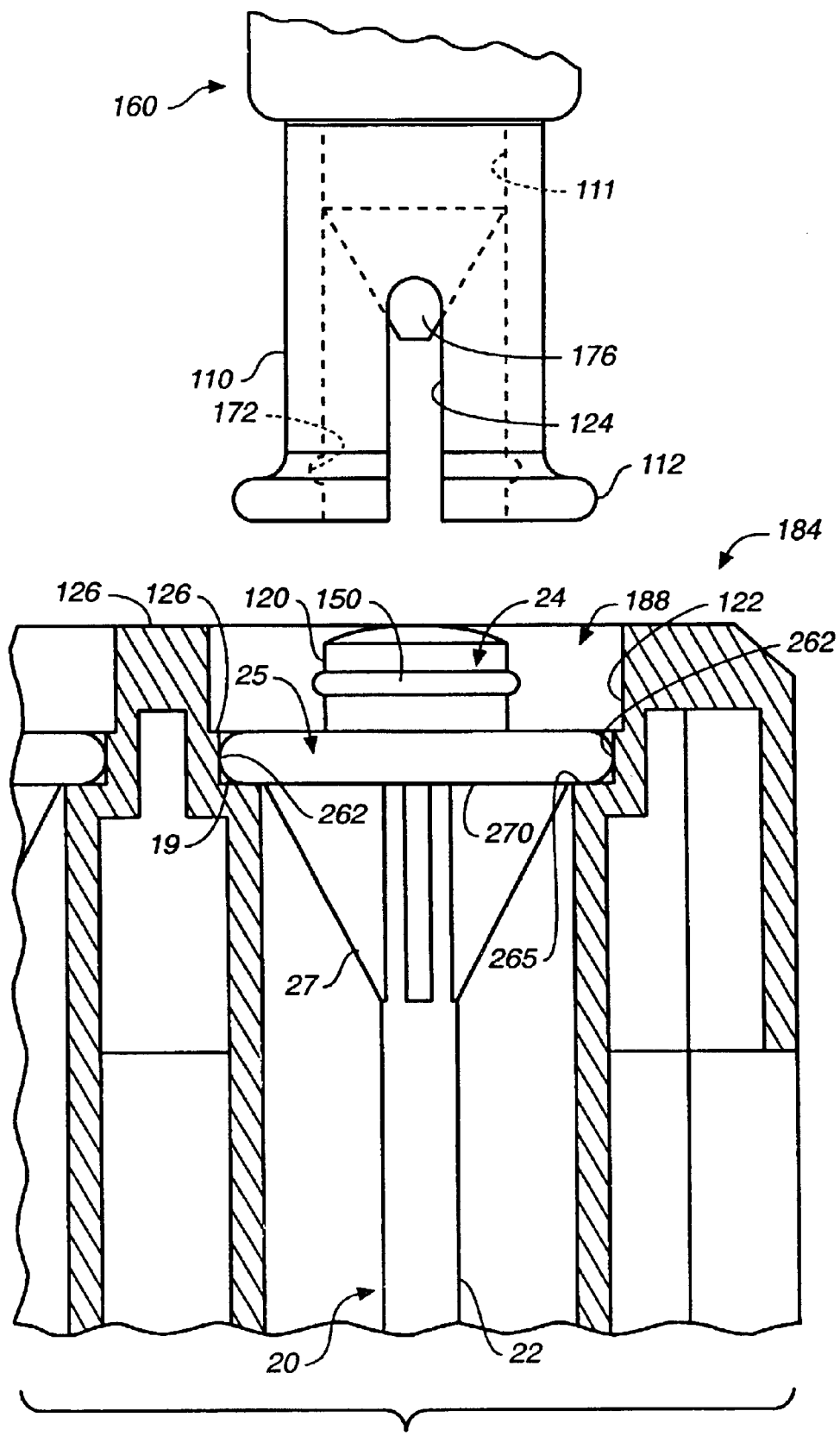
FIG._9

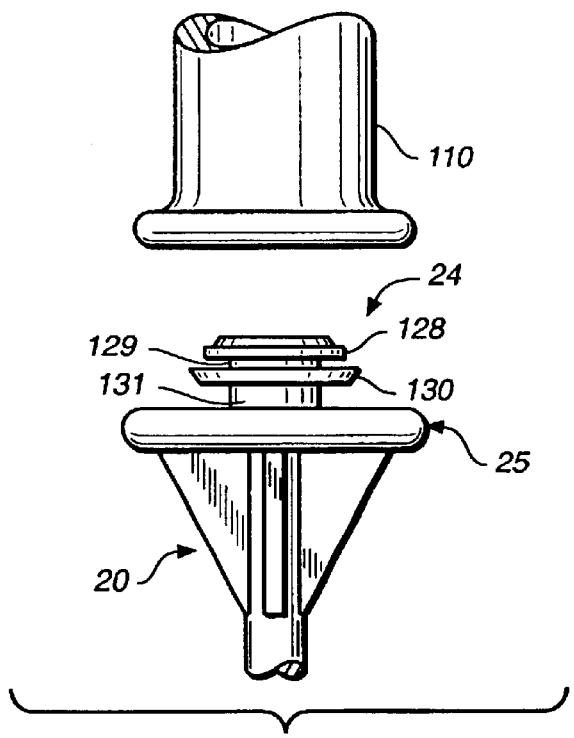
FIG._10A
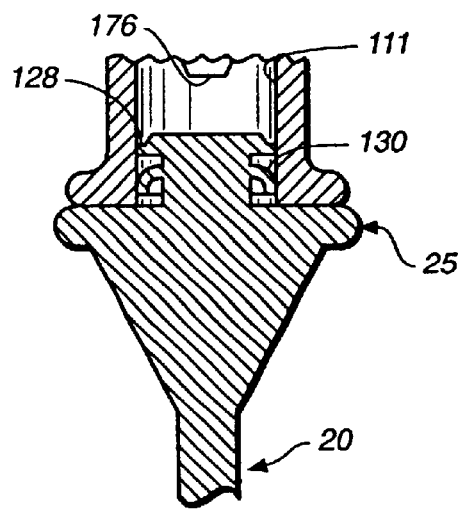
FIG._10B
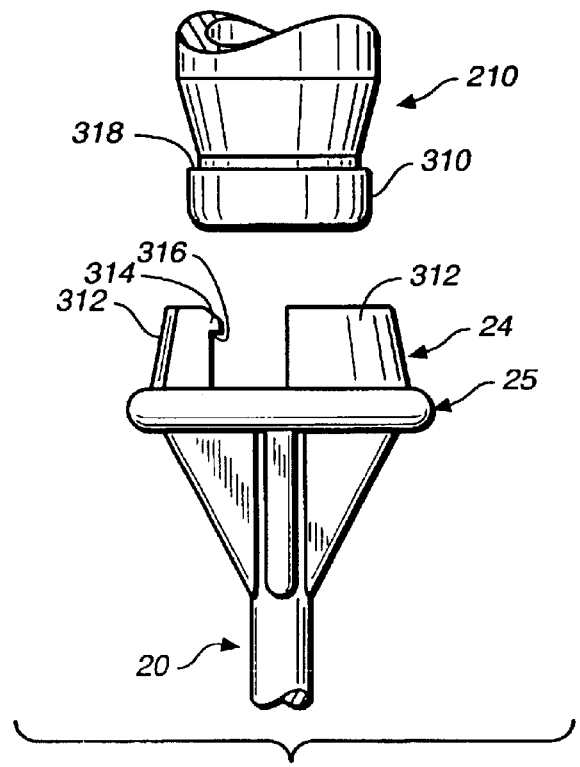
FIG._11A
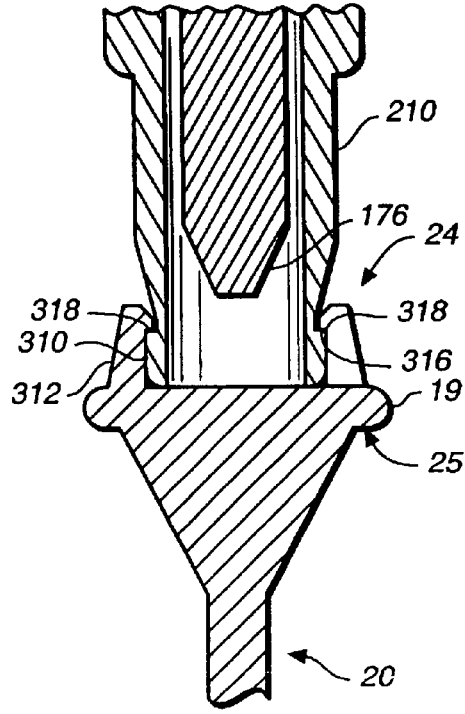
FIG._11B

INOCULATION STORAGE ASSEMBLY AND METHOD FOR USE THEREOF

BACKGROUND OF THE INVENTION

1. Field of the Invention

This invention relates, in general, to inoculation storage devices and more particularly to apparatus and methods used to store and preserve the sterility of inoculation devices.

2. Description of Related Art

U.S. Pat. No. 5,330,899 to DeVaughn shows an inoculation storage assembly and method of preserving the sterility of inoculation loops and streaking needles. The DeVaughn patent discloses a storage assembly or rack having a sheet-like cover positioned across a plurality of openings to seal the cavities and to retain inoculation devices in the cavities in a sterile condition.

As the biotechnology, pharmaceutical and related industries experience unprecedented growth, laboratory research and development proportionately expands. Research precision has become increasingly important, often distinguishing a laboratory's efforts. Through research evolution, research apparatus and techniques, once thought to represent the industry standard, are continually being replaced by better, more efficient and accurate apparatus and techniques.

Typically, after a desired microorganism has been successfully incubated in a nutrient broth substance, it is necessary to colonized the micro-organism so that the particular strain can be identified, researched or be the subject of experimentation. This procedure requires extracting a predetermined quantity of the inoculant from the broth and implanting or inoculating a nutrient medium, or blood agar, so that the microorganism can be grown under more controlled conditions. Using an inoculation device having an inoculating end, which is usually either needle-shaped or a loop, an approximate quantity of the cultured broth may be withdrawn from the broth by immersing the inoculating end in the broth. Subsequently, the inoculant is spread and implanted in the nutrient rich medium (agar) by contacting the inoculating end with the nutrient. Growth is stimulated by incubating the nutrient, for example, at approximately 37 degree C. which simulates body temperature. This incubation period, depending on the rate of growth of the micro-organism which in some cases doubles every 20 minutes, is typically 24 hours. Subsequently, the colonized microorganism may be identified, studied or be the subject of experimentation.

Inoculation tools, in general, have not changed radically since the introduction of the inoculation loop and streaking needle. Earlier inoculation devices were comprised of metallic wires or needles. Often platinum or silver were used because of their high conductive resistance. Metallic inoculation devices usually require sterilization before each use so that the inoculant would not be contaminated by the growth or existence of other contaminating organisms or bacteria carried by the inoculating ends. By placing the inoculating end in an open flame, such as a Bunsen burner, until the end becomes red hot, the loop or needle could be sterilized. The research technician must then wait for the loop to air cool.

Metallic inoculating loops and needles are still in use today. One problem associated with these devices is that this technique is generally time consuming. Often, several different types of microorganism colonies are being cultured consecutively. Valuable time is expended because the inoculating end must be sterilized after contact with each different inoculant or nutrient. Thus, the technician must complete the entire sterilization cycle after each use. Furthermore, since the metallic ends are held over an open flame, the length of the inoculating device must be fairly long to prevent burning the technician. Moreover, insulated handles are often required as a precaution and for ease of handling. Storage, however, becomes problematic when the devices are too long. Finally, materials such as platinum and silver, which are used because of their high conductivity, are undesirably costly. This cost factor is particularly important if one tries to overcome the time delay problems by using multiple metallic inoculation loops or needles.

More recently, plastic inoculating devices have begun to replace metallic inoculating devices. While such plastic inoculation devices have greatly decreased manufacturing cost, sterilization has become a problem. Heat sterilization over an open flame, of course, is inappropriate because the inoculating ends would either melt or substantially deform. Therefore, the inoculation devices must be sterilized by irradiation with radio-isotopes or an electron beam, or by autoclaving before packaging. Typically, a multitude of inoculating loops and needles are sterilized and then packaged in storage BAGS, OR THROUGH ONE MANUFACTURER, Bio-Plas, Inc. of San Francisco, Calif., in a storage rack or container.

These approaches have presented their own problems. Once the bag or rack is opened, all the inoculating devices are subject to becoming contaminated with time or if they are touched. The bag or rack of inoculating devices must be used completely or there is a risk of inoculating future mediums with contaminated inoculants.

This loss of sterilization may be partially overcome by packaging the plastic inoculation devices individually and then sterilizing them. While individual packaging has been satisfactory for most uses, again, however, the loops or needles often become contaminated upon removal from the package. Moreover, removal from each individual package becomes tedious and time consuming, requiring repeated openings of individual containers. Storage also becomes problematic when these devices are amassed in bulk and individual packaging increases cost.

In U.S. Pa. No. 5,330,899 the loss of sterilization problem was overcome by packaging loops and needles in a storage rack having a frangible sheet positioned across the openings of the cavities storing the loops or needles to seal them and to retain the inoculation devices in the cavities. This technique requires the addition of the sheet-like cover to seal and retain the inoculation devices and puncturing of the cover by the inoculation gripping device for each loop or needle.

What is needed is a method and apparatus which overcomes the above and other disadvantages of known inoculation storage assemblies.

SUMMARY OF THE INVENTION

In summary, one aspect of the present invention is directed to a method of storing and dispensing an inoculation device having a sterile inoculation end and a seal carried by the inoculation device for sealing the inoculation device in a sterile cavity in a storage container or rack, comprising the steps of engaging the device, withdrawing it from the rack and optionally releasing it. The engaging step is accomplished by engaging a gripping section of the inoculation device with a handling tool to releasably couple the handling tool to the grasping section of the inoculation device. The withdrawing step is accomplished by withdrawing the inoculation device from the cavity to unseal the seal carried by the inoculation device from the cavity and withdraw the inoculation device and the seal from the cavity for use. Finally, an optional releasing step is provided by releasing the inoculation device from the handling tool by displacing the inoculation device with an extendable member carried by the handling tool until the inoculation device is released from the handling tool.

Another aspect of the present invention is directed to an inoculation kit assembly comprising at least one inoculation device, a storage container, and a handling tool. The inoculation device including an elongated member having a gripping section, an inoculation section, and a seal carried by the elongated member, the seal having a surface formed for sealed engagement against the storage container. The storage container includes at least one cavity having an opening and a seal engagement portion dimensioned to receive and seal against the seal carried by the inoculation device. The inoculation device is mounted in sealed relation with the seal engagement portion for sealing the inoculation end in a sterile condition in the cavity. A handling tool is provided that is. capable of engagement with the gripping section of the inoculation device for releasable grasping of the inoculation device.

Accordingly, the present invention facilitates controlled handling and management of the inoculation device, while further, maintaining the inoculation section or end of the inoculation device out of contact with unsterile portions of the storage container.

Advantageously, the present invention does not require a frangible covering sheet to preserve the sterility of the inoculation end of the inoculation device. Thus, the present invention simplifies manufacturing and use of the inoculation assembly and/or its components.

The calibrated inoculation storage assembly and method for use thereof of the present invention has other features and advantages which will be apparent from, or are set forth in more detail in, the accompanying drawings, which are incorporated in and form a part of this specification, and the following Best Mode of Carrying out the Invention, which together serve to explain the principles of the present invention.

DESCRIPTION OF THE DRAWING

FIG. 1 is an enlarged top plan view, in partial cross section, of an inoculation loop constructed in accordance with the present invention.

FIG. 2 is a side elevation view, in partial cross section, of the inoculation loop of FIG. 1.

FIG. 3 is an enlarged top plan view, of a streaking needle having a modified gripping section in accordance with the present invention.

FIG. 4 is a side elevation view, in cross section, of a handling tool having a gripping end configured for use with the inoculation device of FIG. 3.

FIG. 5 is an enlarged, fragmentary, side elevation view, in partial cross section, showing the releasable engagement between the handling tool and the inoculation device of FIG. 3.

FIG. 6 is a reduced, top perspective view of the inoculation storage rack or container as constructed in accordance with the present invention.

FIG. 7 is an end elevation view in cross section of the inoculation container of FIG. 6.

FIG. 8 is a top perspective view, partially broken away, of an inoculation kit assembly including an inoculation loop, a storage container, and a handling tool constructed in accordance with FIG. 9.

FIG. 9 is an enlarged fragmentary side elevation view, in cross section of inoculation loop of FIGS. 1 and 2 showing sealing therebetween and a handling tool having a modified gripping end.

FIGS. 10A–10B are fragmentary, side elevation views, in partial cross section, illustrating a further alternative embodiment of the inoculation device gripping end and the releasable engagement between a further modified handling tool.

FIGS. 11A–11B are fragmentary, side elevation views, in partial cross section, illustrating still a further alternative embodiment of the inoculation device gripping end and the releasable engagement between a further modified handling tool.

BEST MODE OF CARRYING OUT THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to those embodiments. On the contrary, the invention is intended to cover alternatives, modifications and equivalents, which may be included within the spirit and scope of the invention as defined by the appended claims.

Turning now to the drawings, wherein like components are designated by like reference numerals throughout the various figures, attention is directed to FIG. 1, where an inoculating device, generally designated 20, is illustrated. Inoculating device 20 includes or is formed as an elongated member 22 having a gripping section 24, an inoculation section 26 disposed on one end thereof, and an annular rib or ring seal 25 proximate an opposite end of elongated member 22. The seal may be an annular or circular seal 25 extending radially outward from the longitudinal axis of elongated member 22, and preferably includes an arcuate end surface 19 so as to act in the same manner as an 0-ring seal when brought into contact with a cylindrical sealing surface. Other shapes are possible if the sealing surface in the storage rack is matingly formed. A plurality of bracing flanges 27 extend between the member 22 and seal 25 to assist in guiding insertion of the inoculation device into the storage rack.

Preferably, inoculating device 20 is formed monolithically by injection molding, for example, from polypropylene, which is suitable for autoclaving. It is conceivable, however, that the inoculation device of the present invention may be metallic or formed by other techniques or with other materials.

In one embodiment, inoculating section 26 is in the form of an inoculation loop 28, as represented in FIGS. 1 and 2. Loop 28 is capable of dispensing a predetermined inoculant volume, depending on the size of loop 28. Loop sizes of 1 and 10 microliters are most frequently used, but other sizes may be employed. Loop 28 includes an aperture 30 extending therethrough which retains the inoculant when immersed therein. Inoculation loops of the shape are generally known in the art.

An alternative embodiment of inoculation end 26 of inoculation device 20 is the streaking needle in which end 26 is formed as a needle-shaped end 29, as shown in FIG. 3. Needle-shaped end 29 also is broadly known in the art, and may be used in conjunction with the storage assembly of the present invention.

As shown in FIG. 1, gripping section 24 preferably is formed with cylindrical or rod-like gripping section 24 whereby a handling tool may be used that is dimensioned to slidably telescope over the gripping section 24 and frictionally grip the same. As will be described in more detail in connection with FIG. 9, it is preferable that gripping section 24 include a rib 150 (not shown in FIG. 1, but shown in FIG. 9), or less preferably a groove, which cooperates with a complimentary structure in the gripping tool or handle.

An alternative embodiment of the gripping section also is shown in FIG. 3, wherein gripping section 24 is formed as a substantially cylindrical socket or tubular structure 32 which preferably, but not necessarily, includes a slight taper inward in the mid-section thereof. The longitudinal axis of socket 32 is concentric with the longitudinal axis of elongated member 22. Positioned between gripping section 24 and the inoculation end 26 of elongated member 22 is an annular or circular seal 25 extending radially outward from the body of elongated member 22. Circular seal 25 includes transverse backwall 40 which defines one end of socket 32. Backwall 40 may be substantially planar and oriented substantially perpendicular to the longitudinal axis of elongated member 22. As shown in FIG. 3, socket 32 has an annular rib 50 protruding inwardly in the socket.

In one aspect of the present invention, a releasable handling tool or handle for the inoculation devices, generally designated 60 and shown in FIG. 4, is provided which permits the research technician to easily grip and manually control inoculation device 20 without contaminating inoculating end 26. Handling tool 60 is formed for releasable securement to inoculation device 20 by coupling to gripping section 25 of inoculation device 20.

Handling tool 60 preferably includes an elongated body 62 similar in dimension to a ball-point pen. On one end of elongated body 62 is an inoculation device gripping end 64. According to one embodiment inoculation device gripping end 64 is dimensioned to be telescopically inserted into socket 32, shown in FIG. 3. This insertion produces interengagement of rib 50 in socket 32 with a groove 72 on gripping end 64 of the handle to firmly couple the elongated body of inoculation device 20 to handling tool 60. Accordingly, elongated body 22 of inoculation device 20 can be formed to proportionately shorter than otherwise would be the case since handling tool 60 will extend the operating length of the assembly. In the preferred embodiment, elongated inoculation device 20 can be approximately 3.5 inches in length. This relatively short length will facilitate efficient storage of inoculation devices 20, as will be described below.

Handling tool 60 is adapted for securing engagement with inoculation device 20 and for releasable coupling to section 24 of the inoculation device. As shown in FIG. 5, gripping end 64 of handling tool 60 includes a cylindrical engaging portion 66 dimensioned to snugly and slidably engage front wall portion 48 of socket 32. Furthermore, integrally formed with and protruding from the end of cylindrical engaging portion 66 is a frustoconical portion 68 dimensioned to snugly and slidably engage intermediate inner wall portion 54 of socket 32. The degree of inward inclination of frustoconical portion 68 is substantially similar to the degree of inward inclination of frustoconical section 54 of socket 32. Accordingly, upon telescopic engagement between tool end 64 and gripping section 24 in the direction of arrow 74 in FIG. 5, portion 68 either substantially mates with or preferably slightly frictionally wedges against frustoconical inner wall portion 54 of socket 32. Similarly, the circumferential outer wall of cylindrical engaging portion 66 slidably mates with front wall portion 48 of the socket. The insertion of tool end 64 into socket 32 is limited by the wedging contact between frustoconical portion 68 and frustoconical inner wall portion 54, and by interengagement of ridge 50 and groove 72. Thus, as tool groove 72 is urged over socket rib 50, tool frustoconical surface 68 is held against frustoconical socket surface 54 to produce a tight and stable coupling between the inoculation device and handling tool. This relatively simple "snap-fit" complementary arrangement provides a stable, releasably coupling of inoculation device 20 to handling tool 60. Such a simple arrangement between these two unitary "snap-fit" parts (i.e., tool end 64 and gripping section 24) minimizes coupling efforts and eliminates moving parts. More importantly, this arrangement facilitates coupling by a simple insertion of the tool into the inoculation device and thereby reduces the potential for contamination of inoculating end 26 which could occur through unintentional contact during a more complex manipulation of components.

It will be appreciated that a reversal of snap-fitting or detent parts could be employed. Thus, socket all portion 48 could define an annular recess portion (not shown) extending radially outward from socket 32. The annular recess portion would be formed to matingly cooperate with annular retaining rib (not shown) on tool end 64.

To release inoculation device 20 from handling tool 60, the interengagement between tool end 64 and gripping section 24 must be overcome. Therefore, means for providing a separating force pushing or pulling inoculation device 20 and handling tool 60 in opposite axial directions is desirable. In the preferred embodiment, an extendable tip 76 may be projected from tool end 64 and which can engage gripping section 24. Tip 76 is positioned in a normally retracted condition and is reciprocally mounted inside tool body 62 so as to be extendable in the axial direction of arrow 74. Accordingly, to release inoculation device 20 from handling tool 60, tip 76 is urged forward until it contacts transverse wall 40 of gripping section 24. Tip 76 presses against wall 40 until the reaction or separating force overcomes the detent forces of rib 50 and groove 72 between tool end 64 and gripping section 24, at which point inoculation device 20 releases from handling tool 60.

Tip 76 is coupled to a shat 78 centrally positioned longitudinally through elongated body 62 of handling tool 60. Again, reminiscent of a ball-point pen, shaft 78 is slidably reciprocatable through elongated body 62 so that tip 76 may be extendable from the distal end of engaging end 64 by pressing manually engageable button end 82. The details of construction of the preferred handling tool are set forth in U.S. Pat. No. 6,245,559, which is incorporated in its entirety herein, and such details will not be further set forth.

Turning now to FIGS. 6 and 7, a storage rack or container of the present invention will be described. Briefly, a plurality of inoculation devices 20 are stored in a rack or container, generally designated 84, which includes a plurality of storage cavities 86 dimensioned for individual storage of each inoculation device 20. Individual cavities 86 may be aligned in a row and column matrix for efficient grouping. Each cavity includes a sealing surface, in this case a substantially cylindrical socket (FIG. 7) for sealingly engaging seal 25 of an inoculation device 20. Substantially cylindrical socket 162 preferably, but not necessarily, includes a slight taper inward (e.g., a 1 degree taper) from open upper end or opening 88, which may be chamfered at 89, to inward step 165, which limits axial displacement of inoculation device within cavity 86. A lower cavity portion 163 extends from step 165 to the distal end of cavity 86, which can be rounded. Lower cavity portion 163 may be substantially cylindrical, but in the illustrated embodiment is slightly tapered to facilitate mold release.

In the embodiment shown in FIG. 7, seal 25 protrudes toward slightly tapered seal contact surface 162. The longitudinal axis of cavity 86 is concentric with the longitudinal axis of elongated member 22. The annular or circular seal 25 extends radially outward from the longitudinal axis of elongated member 22 for sealing engagement with seal contact surface 162, and as inoculation device 20 is inserted into cavity 86 to preserve the sterile environment inside cavity 86 below the seal. Seal 25 progressively is urged into a sealing interference fit with surface 162 in order to seal against the same. If seal contact surface 162 were cylindrical chamfer 89 would allow a slightly larger seal 25 (for example, at least 0.003 inches in diameter)to be urged into the cavity until step 165 was reached.

Annular shoulder or step 165 also prevents forcing of the inoculation device downwardly in the rack when the handling tool is urged into socket 32. One should appreciate that an annular shoulder 165 is not required to limit axial motion since one or more protrusions extending inwardly from the wall 162 would also limit the depth to which the inoculation device may be inserted. An annular wall 165, however can supplement the seal formed between seal 25 and wall 162.

Cavity 86 is preferably dimensioned to receive and store inoculation device with gripping section 24 positioned proximate cavity opening 88. Cavity lower portion 163 is dimensioned to receive elongated body 22 and inoculating end section 26, either a loop end or a needle end. Container 84, with inoculation section 26 of inoculation device 20 sealed within lower portion 163 of cavity 86 may be sterilized at the packaging facility, for example, by autoclaving or by irradiation with radioisotopes or by an electron beam. The inner walls of lower cavity portion 163, lower surface of annular seal 25, elongated member 22, and inoculation section 26 of the inoculation device all will be sterilized at packaging. The portion of surface 162 above seal 25 gripping section 24, and upper surface of annular seal 25 may be non-sterile and may be handled without affecting the sterility of elongated member 22. It will be appreciated, however, that they will be initially sterilized during sterilization of the rest of the storage assembly. Moreover, storage rack 84 optionally may include a removable plastic dust cover (not shown) which seats on shoulder 91 so as to cover all of cavity openings 88 and reduce the likelihood of contamination of even the non-sterile portions of the assembly. A further optional structure can be a frangible sealing film which extends over all the rack cavities and is penetrated by the handle. Such a film is not required by reason of seal 25 between the loop/needles and the cavities, and would add back the cost saving resulting from the provision of a seal 25 carried by each inoculation device.

Turning now to FIG. 8 an alternative embodiment of the present storage rack is shown which is particularly well suited for use with inoculation devices 20 having gripping sections 24 as shown in FIGS. 1 and 2. In fact the storage rack of FIG. 8 and the gripping or coupling ends 24 of FIGS. 1 and 2 are preferred as compared to the rack of FIGS. 6 and 7 because the overall height of the storage rack, and thus the plastic or metal require to form the same has been reduced.

In FIGS. 8 and 9 storage rack assembly 184 has a plurality of inoculation device receiving cavities 186 with upwardly facing openings 188 dimensioned to receive inoculation devices 20, here shown as inoculation loops as illustrated in FIGS. 1 and 2. In the rack of FIGS. 8 and 9, however, seal contact surface 262 against which annular seal 25 engages is located axially much closer to opening 188 than was true for rack 84 used to store inoculation devices with socket type gripping ends 24. Moreover, seal surface 262 is much shorter so that the overall height dimension of rack 184 is less than rack 84.

The inoculation handling tool 160 also has been modified from handle 60 to releasably grip or couple with gripping end 24 of the FIGS. 1 and 2 inoculation device. Tool 160 includes a cylindrical end 110 with a tool inner bore 111 dimensioned to snugly and slidably engage outer wall portion 120 of gripping section 24 of the inoculation device. Furthermore, monolithically formed with and protruding radially from the end distal of cylindrical engaging portion 110 is an annular guide lip 112 which can be dimensioned to guide the tool as it enters cylindrical section 122 of cavity 186. Also preferably provided on gripping section 24 is an annular radially protruding rib 150 that will snap into, and matingly engage, an annular groove 172 in the wall defining bore 111. Thus, as cylindrical end 110 of the handling tool is urged down over gripping section 24, tool bore 111 slides over surface 120 until groove 172 snaps over rib 150. Tool end 110 can be slotted at 124 to permit resilient outward displacement and snapping back as the end of bore 111 passes over rib 150. Gripping or coupling section 24 is firmly coupled to the tool with a fit that permits the handle to manipulate the inoculation loop in a controlled manner.

Release of the inoculation tool from either rack 84 or rack 184 can be facilitated by gently rocking handle 60 or 160 from side-to-side relative to the longitudinal axis of the inoculation device 20. This tilting or rocking of handle 60 displaces seal 25 upwardly along tapered wall 162 of the rack 84, and displaces seal 25 upwardly over step 126 between cylindrical walls 122 and 262 to relatively immediately release seal 25 from rack 184.

Again rack 184 includes an annular shoulder or step 265 that limits downward movement of inoculation device 20 by engaging downwardly facing wall 270 of seal 25.

Release of handling tool 160 from gripping section 24 is similar to tool 60. A reciprocally mounted plunger having an inoculation device engaging end 176 can be used to drive the rib 150 out of groove 172 as slot 124 permits resilient outward displacement of opposite sides of tool end 110.

FIGS. 10A and 10B illustrate a modified gripping section 24 formed and dimensioned to be snugly and slidably engaged by a non-grooved tool bore 111. This modified gripping or coupling end 24 can include a cylindrical guide rib 128, a first groove 129 and a second groove 131. Radially extended between grooves 129 and 131 is a flexible cylindrical annular flange 130. Flange 130 extends radially outward from the gripping section to flexibly engage the wall defining tool bore 111, as best may be seen in FIG. 10B. Interengagement of bore 111 against guide rib 128 and flexible cylindrical flange 130 produces a tight and stable coupling between inoculation device 20 and the handling tool so that the assembly can be manipulated easily by the user as a unitary device. This relatively simple resiliently biased flange produces a "frictional-fit" which is stable and which releasably couples inoculation device 20 to the handling tool. Release of the tool end and the gripping section by plunger end 176 is similar to other embodiments described herein, and tool end 110 need not be slotted since flange 130 will do the resilient flexing.

In FIGS. 11A and 11 modified gripping tool end 210 includes a stepped exterior surface housing extending to a raised annular rib or land 310. The releasably engagement is provided by at least two, and preferably three or more, latch fingers 312 which extend axially from seal rib or ring 25. Fingers 312 form an open socket for receiving tool end 210.

Each latch finger 312 is constructed as an arm which extends from a seal 25 to an inward projection or hook 314. An inner shoulder 316 of projection 314 is formed and dimensioned to releasably engage or snap over upwardly facing shoulder 318 of land 310. Further, engagement and release of the inoculation device using tool end 176 and resilient outward displacement of hook finger 312 is similar to other embodiments described herein.

Container or racks 84,184 are preferably formed of a fairly rigid material, and most preferably a polypropylene plastic. It will be noted, however, that container racks 84,184 may be composed of a metallic material or other plastics without departing from the true spirit and nature of the present invention. Furthermore, it will be appreciated that container racks 84,184 are of sufficient weight to maintain gravity biased stability against a working surface during use without requiring manual engagement thereof by the user. Only one hand need be used by the technician to insert the handling tool to couple it to the gripping section of the inoculation device 24, and to withdraw inoculation device 20 from the rack cavity by gently rocking the tool to release the seal. The weight of container racks 84,184 allows rocking and withdrawal without tipping over or lifting up of the rack off the working surface. This is true even if only one inoculating device 20 remains stored in the storage rack.

In the present invention, an inoculation kit assembly is provided which permits quick and easy access to the individual inoculation devices while preserving sterility of each of the inoculating ends. The handling tool end quickly and accurately grips or couples to a gripping section of the inoculation device and allows easy removal of the inoculation device from rack cavity while maintaining inoculation device out of contact with unsterile portions of the rack. The used inoculation device then can be easily ejected from the tool by pressing a plunger button, and the procedure can be repeated quickly and efficiently, while always preserving sterility of inoculating end.

For convenience in explanation and accurate definition in the specification and appended claims, the terms "up" or "upper," "down" or "lower," "inside" and "outside" are used to describe features of the present invention with reference to the positions of such features as displayed in the figures.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

What is claimed is:

1. A method of dispensing an inoculation device mounted in sealed relation to a sterile cavity in a storage container, comprising the steps of:
    selecting an inoculation device having a sterile inoculation end and a seal carried thereby sealing the inoculation end in the sterile cavity;
    engaging a gripping section of the inoculation device with a handling tool to releasably couple the handling tool to the gripping section; and
    withdrawing the inoculation device and the seal from the cavity to unseal the inoculation device from the cavity.

2. The method of claim 1 wherein,
    the selecting step is accomplished by selecting an inoculation device having a seal dimensioned for interference fit with a sealing surface of the cavity.

3. The method of claim 2 wherein,
    the withdrawing step is accomplished by tilting the inoculation device to facilitate breaking of the seal and withdrawal from the cavity.

4. The method of claim 1 wherein,
    the step of engaging is accomplished by engaging a gripping section of the inoculation device above the seal with the handling tool to releasably couple the handling tool to the gripping section.

5. The method of claim 4 wherein,
    the step of engaging is accomplished by urging the handling tool toward the inoculation device until the inoculation device is releasably coupled to the handling tool.

6. The method of claim 1, further comprising the step of:
    releasing the inoculation device from the handling tool by displacing an extendible member in the handling tool to separate the inoculation device from the handling tool.

7. The method of claim 1 wherein,
    the engaging and withdrawing steps are accomplished through an uncovered opening to the cavity.

8. An inoculation storage assembly comprising:
    an inoculation device including an elongated member having a gripping section, an inoculation end, and a seal carried by the elongated member, the seal having a surface formed for sealed engagement against a seal contact surface; and
    a storage container including the cavity having an opening thereto and a seal contact surface dimensioned for sealing of the seal thereagainst, the inoculation device being mounted in sealed relation with the seal contact surface.

9. The inoculation storage assembly as defined in claim 8, and
    a handling tool formed for engagement with the gripping section of the inoculation device for releasable grasping of the gripping section while the inoculation device is in the cavity.

10. The inoculation storage assembly as defined in claim 9 wherein,
    the inoculation end and the cavity below the seal are sterile.

11. The inoculation storage assembly as defined in claim 9 wherein,
    the seal contact surface is an inwardly tapered frustoconical surface formed to progressively increase the interference fit between the seal and the seal contact surface.

12. The inoculation storage assembly as defined in claim 11 wherein,
    the seal is a radially projecting annular ring on the inoculation device having an arcuate end surface.

13. The inoculation storage assembly as defined in claim 9 wherein,
    the handling tool includes a protruding end; and
    the gripping section includes a socket dimensioned to slidably receive the protruding end for frictional coupling therebetween.

14. The inoculation storage assembly as defined in claim 9 wherein, the handling tool includes a bore in an end thereof; and the gripping section includes an axially protruding coupling portion dimensioned to slidably telescope inside said bore and adapted for releasable frictional coupling to the end of the handling tool when positioned in the bore.

15. An inoculation storage assembly comprising:

an inoculation device including an elongated member having a gripping section at one end thereof, an inoculation section at an opposite end thereof and a seal carried by the elongated member proximate the gripping section and between the gripping section and the inoculation section, the seal having an arcuate annular surface formed for sealed engagement against a substantially cylindrical seal contact surface; and a storage container including the cavity having an open upper end and a substantially cylindrical seal contact surface dimensioned to sealingly receive the seal, the inoculation device being mounted in sealed relation with the seal contact surface with the cavity being open above the seal.

16. The inoculation storage assembly as defined in claim 15 wherein, the inoculation device and the cavity below the seal are sterile.

17. The inoculation storage assembly as defined in claim 15 wherein, the inoculation section is one of a loop end and a needle end.

18. The inoculation storage assembly as defined in claim 15 wherein, the arcuate surface of the seal frictionally engages the seal contact surface of the cavity in the manner of an O-ring.

19. The inoculation assembly as defined in claim 15 wherein, the cavity is radially inwardly step at a lowermost portion of the substantially cylindrical seal contact surface by an amount preventing axial displacement of the seal of the inoculating device beyond the step.

20. The inoculation storage assembly as defined in claim 18 wherein, step is provided by an upwardly facing annular shoulder in the cavity, and a downwardly facing shoulder on the seal seats against the shoulder in the cavity.

21. The inoculation storage assembly as defined in claim 15 wherein, the storage container is formed to define a plurality of separate, similarly formed side-by-side cavities each having open upper ends;

a plurality of inoculation devices each formed with a seal thereon adapted for sealing against a portion of a cavity and mounted in seal relation with one of the cavities.

22. The inoculation storage assembly as defined in claim 15 wherein, the gripping section is formed with an annular radially protruding rib formed for cooperative engagement by a handling tool having a matingly formed annular groove.

23. The inoculation storage assembly as defined in claim 15 wherein, the gripping section is formed with a radially extending, resiliently flexible flange dimensioned to be resiliently inwardly and downwardly displaced to frictionally couple to a wall defining a bore in a handling tool.

24. The inoculation storage assembly as defined in claim 15 wherein, the gripping section is formed by a plurality of resiliently displaceable fingers adapted to releasably grip shoulder provided of a handling tool.

25. The inoculation storage assembly as defined in claim 15, and a handling tool adapted to be inserted into the open end of the cavity and to be releasably coupled to the gripping section of the inoculation device above the seal, the handling tool further being adapted to release the seal and to withdraw the inoculation device from the cavity through the open end.

\* \* \* \* \*